United States Patent
Dhaher et al.

(10) Patent No.: US 10,168,262 B2
(45) Date of Patent: Jan. 1, 2019

(54) PRETENSIONER SYSTEM AND METHODS

(71) Applicants: REHABILITATION INSTITUTE OF CHICAGO, Chicago, IL (US); NORTHWESTERN UNIVERSITY, Evanston, IL (US)

(72) Inventors: Yasin Dhaher, Mount Prospect, IL (US); Matthew Patrick, Muncie, IN (US)

(73) Assignees: Rehabilitation Institute of Chicago, Chicago, IL (US); Northwestern University, Evanston, IL (US)

( * ) Notice: Subject to any disclaimer, the term of this patent is extended or adjusted under 35 U.S.C. 154(b) by 0 days.

(21) Appl. No.: 14/569,603

(22) Filed: Dec. 12, 2014

(65) Prior Publication Data

US 2015/0168281 A1 Jun. 18, 2015

Related U.S. Application Data

(60) Provisional application No. 61/915,984, filed on Dec. 13, 2013.

(51) Int. Cl.
*G01L 1/22* (2006.01)
*G01N 3/08* (2006.01)
(Continued)

(52) U.S. Cl.
CPC .............. *G01N 3/08* (2013.01); *A61B 90/06* (2016.02); *G01L 5/102* (2013.01); *A61B 2090/064* (2016.02); *G01N 2203/028* (2013.01)

(58) Field of Classification Search
CPC .......... G01N 3/08; A61B 19/46; A61B 90/06; G01L 5/102
(Continued)

(56) References Cited

U.S. PATENT DOCUMENTS 2,564,150 A * 8/1951 Brown ..................... G01N 3/14
73/862.471
3,791,388 A * 2/1974 Hunter .................. A61L 17/145
264/186
(Continued)

FOREIGN PATENT DOCUMENTS

DE 19716134 A1 * 10/1998 ............. B65H 59/40
EP 1 646 573 B1 7/2009
(Continued)

OTHER PUBLICATIONS

Authors: Vivek Prasad and Shankam Narayana, Title: Novel Method for Dynamic Yarn Tension Measurement and Control in Direct Cabling Process, Date: Dec. 2005, Publisher: North Carolina State University, pp. 122.*
(Continued)

*Primary Examiner* — Lisa Caputo
*Assistant Examiner* — Roger Hernandez-Prewit
(74) *Attorney, Agent, or Firm* — Drinker Biddle & Reath LLP

(57) ABSTRACT

A device and methods for measuring the tension applied to a suture are disclosed. In one embodiment, the device comprises a housing comprising at least one attachment point for attachment of the suture, for the device to hang from the suture when a tension is applied to the suture. The device may also comprise a force sensing unit, contained in the housing and configured to measure the amount of tension applied to the suture.

5 Claims, 9 Drawing Sheets

(51) Int. Cl.
*G01L 5/10* (2006.01)
*A61B 90/00* (2016.01)

(58) Field of Classification Search
USPC ...... 73/826, 862.391, 862.451; 606/144, 148
See application file for complete search history.

(56) References Cited

U.S. PATENT DOCUMENTS

| | | | | |
|---|---|---|---|---|
| 4,043,344 | A * | 8/1977 | Landi et al. | ........... A61L 17/145 |
| | | | | 128/898 |
| 4,587,855 | A * | 5/1986 | Yamada et al. | ........... G01L 5/10 |
| | | | | 73/862.451 |
| 4,950,271 | A | 8/1990 | Lewis et al. | |
| 4,964,862 | A | 10/1990 | Arms | |
| 4,992,778 | A * | 2/1991 | McKeen et al. | ........ B66C 15/00 |
| | | | | 116/212 |
| 5,192,321 | A * | 3/1993 | Strokon | ............. A61B 17/1714 |
| | | | | 606/1 |
| 6,524,240 | B1 * | 2/2003 | Thede | .................... A61B 5/021 |
| | | | | 128/897 |
| 6,949,102 | B2 | 9/2005 | Andrews | |
| 7,326,222 | B2 | 2/2008 | Dreyfuss et al. | |
| 7,329,271 | B2 * | 2/2008 | Koyfman et al. | .......................... |
| | | | | A61B 17/06166 |
| | | | | 606/139 |
| 7,338,492 | B2 * | 3/2008 | Singhatat et al. | . A61B 17/1714 |
| | | | | 128/898 |
| 8,182,495 | B2 | 5/2012 | DiStefano et al. | |
| 8,298,247 | B2 | 10/2012 | Sterrett et al. | |
| 2003/0097885 | A1 * | 5/2003 | Kell | ........ G01L 5/101 |
| | | | | 73/862 |
| 2008/0033549 | A1 | 2/2008 | Marshall et al. | |
| 2008/0275477 | A1 * | 11/2008 | Sterrett et al. | ..... A61B 17/0469 |
| | | | | 606/148 |
| 2013/0238257 | A1 * | 9/2013 | Rajamani et al. | ........ G01L 1/04 |
| | | | | 702/43 |

FOREIGN PATENT DOCUMENTS

| | | | | |
|---|---|---|---|---|
| JP | 10197372 A | * | 7/1998 | ............. B65H 59/40 |
| WO | 2005/014456 A1 | | 2/2005 | |

OTHER PUBLICATIONS

Author: John F. Cummings, PhD, Title: A Miniature Suture Tensiometer for Laparoscopic Applications, Date: Jan. 2000. Publisher: Journal of Investigative Surgery, 13: pp. 253-258.*

Machine Translation of JP10-19732A, Title: Thread Tension Sensor, Date: Jul. 31, 1998, Publisher: JPO and INPIT, pp. 11.*
Machine Tranlation of DE19716134A1, Title: Tension sensor for running yarn, Date: Oct. 22, 1998, Publisher: Espacenet, pp. 14.*
Dienst et al., Anatomy and biomechanics of the anterior cruciate ligament. Orthop Clin North Am 2002;33(4):605-620.
Keene et al., The natural history of meniscal tears in anterior cruciate ligament insufficiency. Am J Sports Med 1993;21:672-679.
Owings et al., Ambulatory and inpatient procedures in the United States 1996. Vital Health Stat Nov. 13, 1998;(139):1-119.
Li et al., Predictors of radiographic knee osteoarthritis after anterior cruciate ligament reconstruction. Am J Sports Med. Dec. 2011;39(12):2595-603. doi: 10.1177/0363546511424720. PubMed. PMID: 22021585.
Nicholas et al., A prospectively randomized double-blind study on the effect of initial graft tension on knee stability after anterior cruciate ligament reconstruction. Am J Sports Med 2004;32(8):, pp. 1-6.
Brady et al, Effects of initial graft tension on the tibiofemoral compressive forces and joint position after anterior cruciate ligament reconstruction. Am J Sports Med 2007;35(3):395-403.
Sherman et al., Graft Tensioning During Knee Ligament Reconstruction: Principles and Practice. J Am Acad Orthop Surg Oct. 2012;20(10):633-645.
O'Neill et al., Anterior cruciate ligament graft tensioning. Is the maximal sustained one-handed pull technique reproducible/ BMC Research Notes 2011, 4:244 (2011), 7pages.
Katsuragi et al., The effect of nonphysiologically high initial tension on the mechanical properties of in situ frozen anterior cruciate ligament in a canine model. Am J Sports Med. Jan.-Feb. 2000;28(1):47-56. PubMed PMID: 10653543.
Witte et al., A transducer for measuring force on surgical sutures. The Canadian Journal of Veterinary Research. 2010; 74:299-304.
Ventura et al., An Implantable Transducer for Measuring Tension in an anterior Cruciate Ligament Graft. Journal of Biomechanical Engineering. Jun. 1998, vol. 120; 327-333.
Albritton et al., TunneLoc Tibial Fixation Surgical Protocol. Biomet Sports Medicine, 2011, 12 pages.
Linvatec, SE Graft Tensioning System: Surgical Technique, Linvatec Corporation, 2003-2004, 11 pages.
Meijer et al., Disposable pulling force sensor for force measurements in surgical sutures, ResearchGate. https://www.researchgate.net/publication/259561840_Disposable_Force_sensors_for surgery, 4 pages.
Horeman et al., Force Sensing in Surgical Sutures. PLOS ONE. Dec. 2013, vol. 8, Issue 12, e84466: 1-12 (2013).
McGuire et al., Evaluation of Posterior Cruciate Ligament Tensioning Device, 2009 IEEE 35th Annual Northeast Bioengineering Conference, Apr. 3-5, 2009, 2 pages.

* cited by examiner

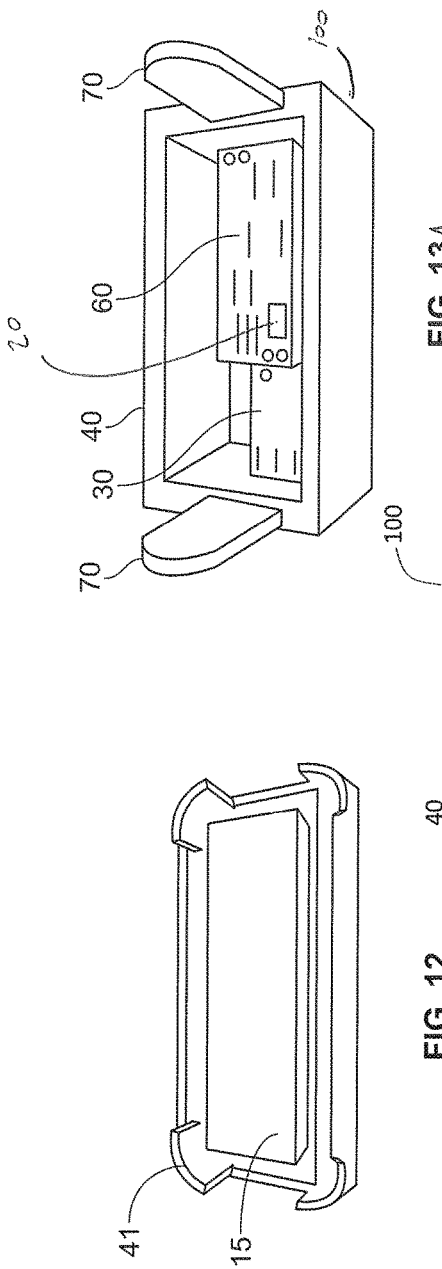
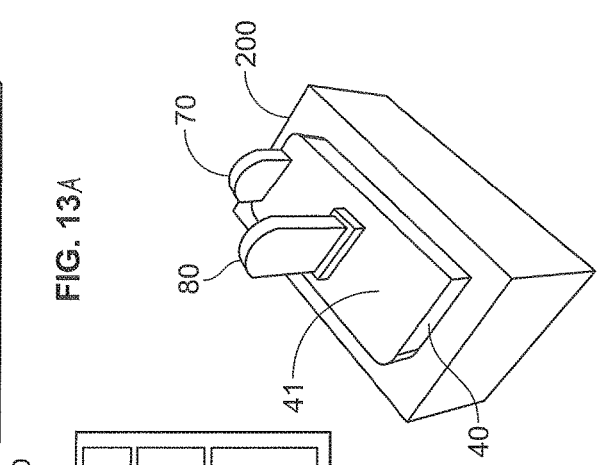
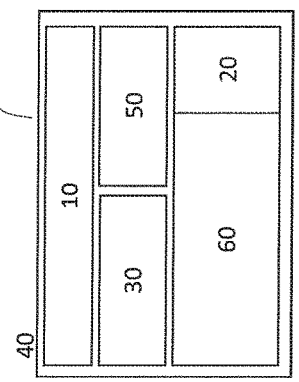
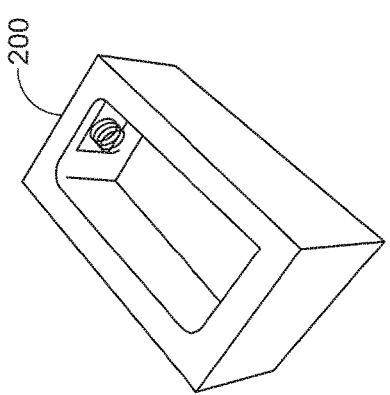
FIG. 13A
FIG. 13B
FIG. 12
FIG. 14
FIG. 15

PRETENSIONER SYSTEM AND METHODS

CROSS-REFERENCE TO RELATED APPLICATIONS

This application claims the priority and benefit to U.S. Provisional Patent Application No. 61/915,984, which is herein incorporated by reference in its entirety.

TECHNICAL FIELD

The present document relates generally to a device for measuring the tension in a suture.

BACKGROUND

The Anterior Cruciate Ligament ("ACL") performs a stabilizing function in the human knee, by resisting anterior translation and medial rotation of the tibia relative to the femur. An injury to this ligament causes instability of the knee joint and increases the likelihood of further damage to the joint such as meniscal tearing. In many instances of ACL injury, reconstructive surgery is utilized as a treatment to allow affected individuals to return to high intensity athletic activity. In the United States alone, over 100,000 cases of ACL reconstructive surgery are performed each year. Additionally, the fact that ACL reconstruction surgeries are mostly performed on young, active individuals, such as athletes and military service personnel, is a cause for concern. A recent large-scale retrospective study has shown that following ACL reconstruction, 39% of patients exhibit radiographic osteoarthritis after an average of 7.8 years after surgery despite reconstruction efforts.

ACL surgery attempts to restore the function of the ACL by restoring the structure of the ligament. The damaged ACL is removed from its attachment points on the femur and tibia of the patient, and is replaced by a surrogate tissue. The most common sources for the ACL replacement tissue are the patient's own patellar tendon, the patient's own hamstring tendon, and ACLs from cadavers. While a variety of techniques are utilized in the surgical protocol, the standard procedure begins with harvesting and preparing the graft tissue, followed by removal of the damaged ACL. Next, tunnels for affixation of the grafted tissue are drilled into the tibia and the femur. The graft is passed through the tibia tunnel and affixed at the tibia. The surgeon must then apply tension to the graft, to affix it to the patient's femur. The surgeon applies this tension by attaching a suture to the graft, and pulling the suture and the graft through the femur tunnel. When the surgeon has applied what he or she believes to be the appropriate tension, and the graft is in the appropriate position in the femur tunnel, the surgeon affixes the graft to the femur.

The amount of tension applied to the graft before it is affixed to the patient—known as "pretension"—is widely variable, dependent on the background, experience, and skills of the surgical team, as well as possible human error. Surgeons with less experience in performing ACL repair may have less ability to judge the prehensive effects of the force they apply to a graft. The effects of an inappropriately tension grafts are detrimental to the function of the knee. Although ACL reconstruction surgeries are very common, there is still no established optimal graft tension, and the clinical evidence for appropriate graft tension is largely inconclusive or lacking. See, e.g., Sherman S L, Chalmers P N, Yanke A B, Bush-Joseph C A, Verma N N, Cole B J, Bach B R Jr: Graft Tensioning During Knee Ligament Reconstruction: Principles and Practice. J Am Acad Orthop Surg October 2012; 20(10):633-645. Part of the reason for the difficulties establishing correct ACL pretension values is the difference in stiffness between native ACL tissue and replacement graft tissue. The stiffness for bone-patellar tendon-bone grafts and hamstring grafts are much greater than the stiffness for native ACL tissue, so there is less tension required in these grafts than is present in the native ACL. For bone-patellar tendon-bone grafts, the stiffness is approximately 1200 N/mm significantly greater than the approximately 800 N/mm stiffness for quadrupled hamstring grafts, and these are both greater than the stiffness of the native ACL, which is less than 200 N/mm.

Inappropriate placement or applied tension of the replacement ACL graft may result in continued knee instability or graft re-tear. See Nicholas S J, D'Amato M J, Mullaney M J, Tyler T F, Kolstad K, McHugh M P: A prospectively randomized double-blind study on the effect of initial graft tension on knee stability after anterior cruciate ligament reconstruction. Am J Sports Med 2004; 32(8):1881-1886; Brady M F, Bradley M P, Fleming B C, Fadale P D, Hulstyn M J, Banerjee R: Effects of initial graft tension on the tibiofemoral compressive forces and joint position after anterior cruciate ligament reconstruction. Am J Sports Med 2007; 35(3):395-403. If a surgical team under-tensions the replacement ACL graft, the patient's knee will not have the same ability as a normal knee. Overtensioning of the ACL graft can cause the graft to tear, which may result in the need for additional surgery. A knee with an inadequately tensioned replacement graft will behave in the same way as an ACL-deficient knee. See, e.g., Nicholas S J, D'Amato M J, Mullaney M J, Tyler T F, Kolstad K, McHugh M P: A prospectively randomized double-blind study on the effect of initial graft tension on knee stability after anterior cruciate ligament reconstruction. Am J Sports Med 2004; 32(8): 1881-1886. Over-tensioned grafts will produce higher contact pressures, which may lead to joint misalignment as well as graft breakdown.

Currently, the preferred method for ACL graft pretensioning is the single-hand pull, which does not allow surgeons to consistently produce the same amount of pretensioning force. See, e.g., O'Neill, Barry J., Fergus J. Byrne, Kieran M. Hirpara, William F. Brennan, Peter E. McHugh, and William Curtin. "Anterior Cruciate Ligament Graft Tensioning. Is the Maximal Sustained One-handed Pull Technique Reproducible?" BMC Research Notes 4.1 (2011): 244. After affixing the femoral end of the graft, tension is applied to the graft before affixing the tibial end by pulling on connecting sutures. This method of tensioning by hand is only as precise as a surgeon's perception of applied force.

DRAWINGS

While the appended claims set forth the features of the present techniques with particularity, these techniques may be best understood from the following detailed description taken in conjunction with the accompanying drawings of which:

FIGS. 1, 2, and 3 illustrate various stages of a graft being affixed to a femur and tibia.

FIG. 12 illustrates a strain gauge bar inserted into a housing lid.

FIG. 13A illustrates electric components placed in a housing of one embodiment of the pretensioner. FIG. 13B is a representation of a force sensing unit, circuit, transmitter, battery, and microcontroller housed in a housing in an embodiment of the pretensioner.

FIG. 14 illustrates an embodiment of a charging unit.

FIG. 15 illustrates an embodiment of the pretensioner connected to an embodiment of the charging unit.

DESCRIPTION

Figure 1:
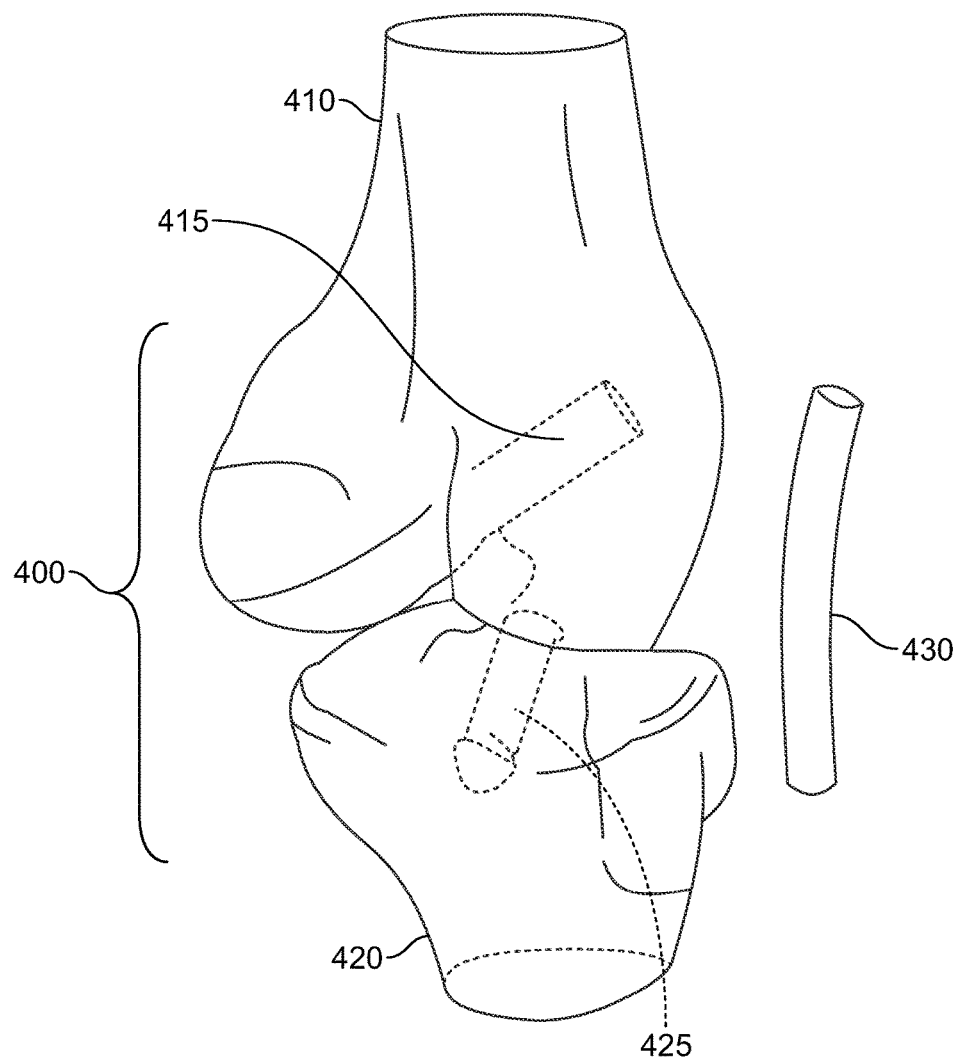

In various embodiments, the systems and methods described herein measure pretension force applied to a tissue graft. In one embodiment, the pretension force is measured by a pretensioner as a function of tension in a suture.

In one embodiment, a device for measuring the tension applied to a suture may comprise a housing comprising at least one attachment point for attachment of the suture, for the device to hang from the suture when a tension is applied to the suture; and a force sensing unit, contained in the housing and configured to measure the amount of tension applied to the suture. The force sensing unit may be positioned below the at least one attachment point, such that the force sensing unit is positioned below the suture when the device hangs from the suture. In one embodiment, the at least one attachment point comprises a first attachment point at a first end of the housing and a second attachment point at a second end of the housing. In one embodiment, the force sensing unit comprises a strain gauge. In one embodiment, the force sensing unit is configured to measure the tension on the suture in amounts as small as 1 Newton. In one embodiment, the force sensing unit is arranged in the housing to provide a tension on the force sensing unit when the device is not hanging from the suture. In one embodiment, the housing further comprises a lid, the device further comprising a member comprising a third attachment point for attachment of the suture at a first end of the member and a second end of the member being engageable with the lid, wherein the force sensing unit is at least partially positioned in the lid. In one embodiment, the second end of the member is engageable with the lid through an opening of the lid. In one embodiment, each of the at least one attachment points may be an opening for the threading of the suture. In one embodiment, the device is part of a kit, the device further comprising a transmitter for transmitting information about the tension applied to the suture, and the kit further comprising a battery, configured to fit in the housing of the device, and a charger for the battery. In one embodiment of the kit, each of the device and the charger has one corner of similar shape, to assist in the proper positioning of the device in the charger.

In another embodiment, the device may comprise a first member, comprising a first attachment point for a suture and positioned within the device so as to transfer tension applied to the suture into movement of the first member; and a force sensing unit, engageable with the first member, for sensing movement of the first member. The device may further comprise a second member having a second attachment point for a suture and a third member having a third attachment point for a suture, wherein the first member is positioned between the second member and the third member. The device may further comprise a transmitter for transmitting information about movement of the first member, and be part of a kit that further comprises a battery, configured to fit in the housing of the device; and a charger for the battery. In one embodiment of the kit, each of the device and the charger has exactly one corner of similar shape, for proper positioning of the device in the charger.

Additionally, a device may be used in a method for measuring the tension applied to a suture. In one embodiment, the method comprises attaching a suture to a graft at a first point of the suture; positioning a device for determining the tension applied to the suture, between the first point and a second point of the suture; applying a tension to the suture at the second point of the suture; and determining the tension applied to the suture using information from the device. In one embodiment, the device comprises a force sensing unit that produces a signal in response to tension in the suture. In one embodiment, the step of applying a tension to the suture is performed after the step of positioning the device. In one embodiment, the step of determining the tension applied to the suture comprises viewing on a display the amount of tension applied, said amount determined based on the information from the device. In one embodiment, the method is used in an ACL surgery. In one embodiment, the method is used in a posterior cruciate ligament ("PCL") surgery.

In an embodiment, a device for measuring the tension applied to a suture may comprise a metal bar having an initial tension; a member, configured to engage at a first point with the suture; and a sensor for detecting an amount of deformation of the metal bar; wherein a tension applied to the suture causes the member to deform the metal bar. In one embodiment, the device may further comprise a housing for the metal bar. In one embodiment, the metal bar is arranged in the housing to provide the initial tension. In one embodiment, the housing comprises an opening for insertion of the member. In one embodiment, the member is configured to deform the metal bar by pushing against the metal bar at a second point and in response to tension applied to the suture. In one embodiment, the sensor is positioned on the side of the metal bar opposite from the second point.

Turning to the drawings, wherein like reference numerals refer to like elements, techniques of the present disclosure are illustrated as being implemented in a suitable environment. The following description is based on embodiments of the claims and should not be taken as limiting the claims with regard to alternative embodiments that are not explicitly described herein.

Figure 3:
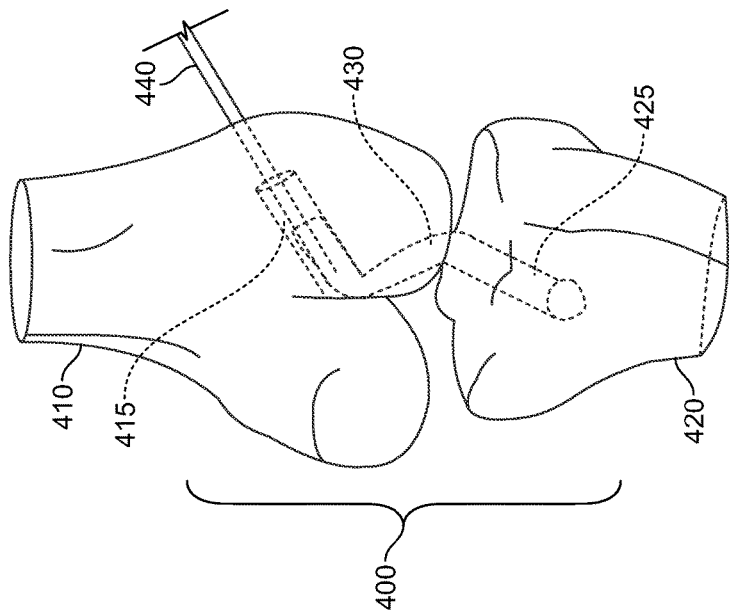
Figure 2:
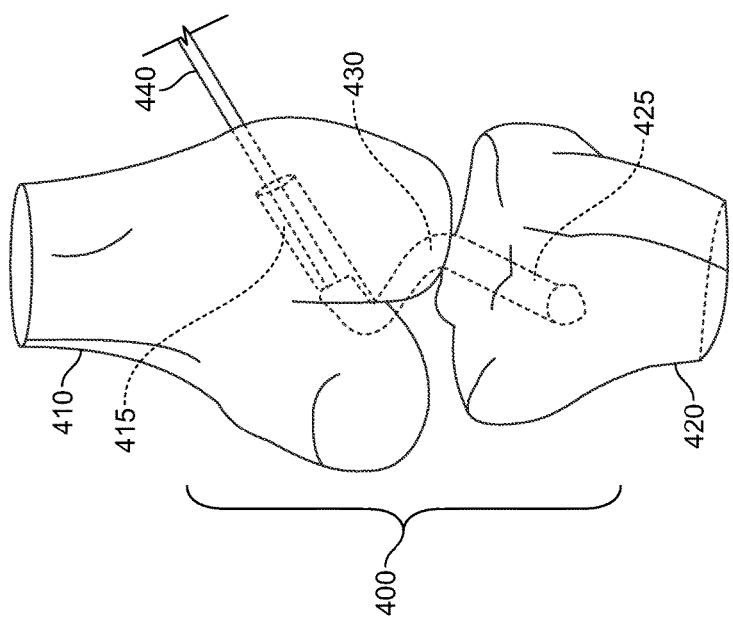

FIG. 1 illustrates a knee 400, femur 410 having femur tunnel 415, and tibia 420 having tibia tunnel 425. FIG. 1 also illustrates graft 430. FIG. 2 illustrates the placement of graft 430 after it has been attached, through tibia tunnel 425, to tibia 420. The top of graft 430 is affixed to suture 440, which extends from the top of graft 430, through femur tunnel 415, and out the back of femur 410. FIG. 3 illustrates graft 430 moving into femur tunnel 415 as the surgeon pulls on suture 440.

Figure 4:
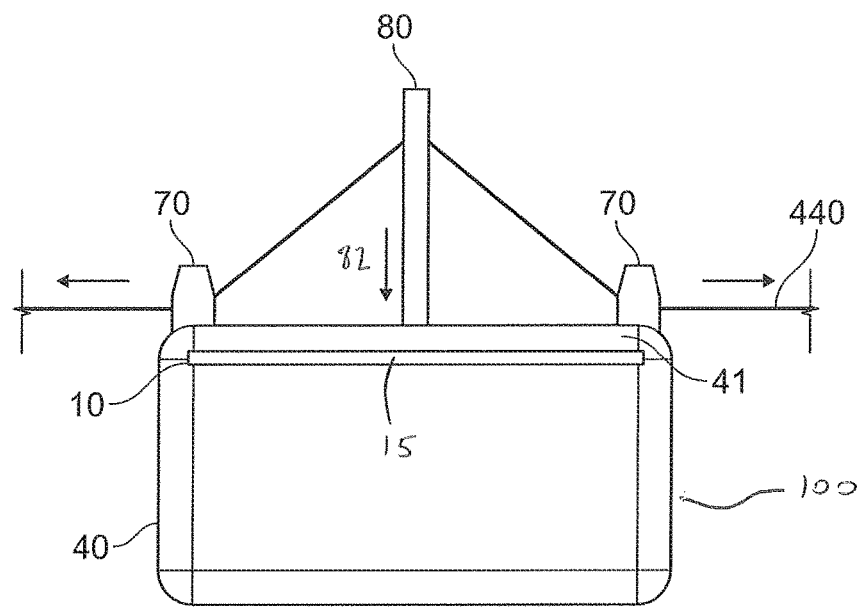
FIG. 4 illustrates a suture threaded through one embodiment of a pretensioner.
Figure 16:
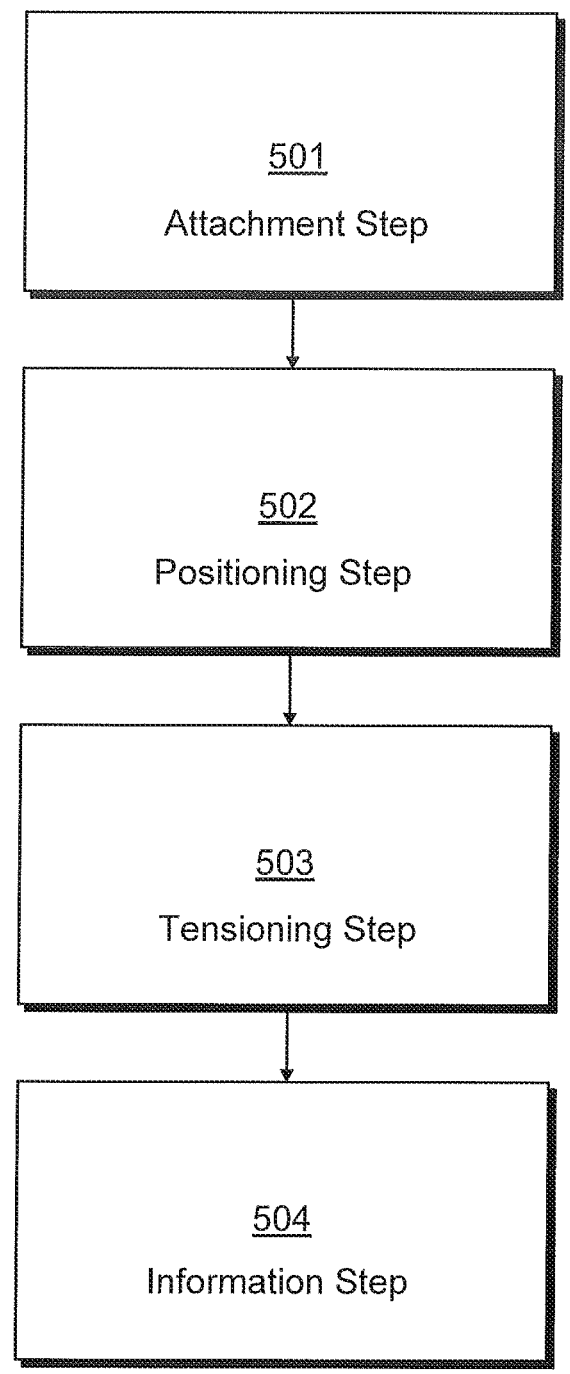
FIG. 16 illustrates one method of using an embodiment of a pretensioner.

By pulling on suture 440, the surgeon creates a tension in suture 440 that reflects the pretension applied to the graft. Suture 440 may be threaded through pretensioner 100, illustrated in FIG. 4, in order to measure the pretension being applied to the graft. As illustrated in FIG. 4, suture 440 is threaded through attachment points 70 and center post 80. As the surgeon pulls on suture 440, pretensioner 100 measures the pretension in the suture and transmits the measure for further analysis and operation. Threading is a simple process and may take less than a minute, allowing the surgeon to focus on the graft pull and the surgery. It is to be understood that there are multiple ways of using the pretensioner 100 based on the above disclosure. One method of using the pretensioner 100 in surgery is provided at FIG. 16. In 501, the suture 440 is attached to the graft at a first point of the suture 440, which may be an end of the suture 440. In 502, the pretensioner 100 is positioned between the first point of the suture 440 and a second point of the suture 440, which may be the position on the suture being pulled by the surgeon. In 503, a tension is applied to the suture at the second point of the suture, for instance, by the surgeon. In 504, the tension applied to the suture is determined using information from pretensioner 100. For example, the physician may view a tablet or other computing device that displays the amount of tension, based on information provided by the pretensioner 100 (such as information provided by the transmitter 30 of pretensioner 100). The physician may apply tension to the suture after positioning the pretensioner 100, or may position the pretensioner 100 after applying tension.

Because the pretensioner 100 hangs off the suture 440 while the surgeon is pulling suture 440, embodiments of the pretensioner 100 may be made of lightweight materials, such as Teflon or other plastic. Additionally, because pretensioner 100 is used in an operating room environment, it should be made of a material that can be sterilized according to standard operating room procedures, such as a plastic. In one embodiment, pretensioner 100 comprises a force sensing unit 10, circuit 20, transmitter 30, battery 50, and microcontroller 60, and is housed in a housing 40, as described in further detail below.

Force Sensing Unit.

Figure 5:
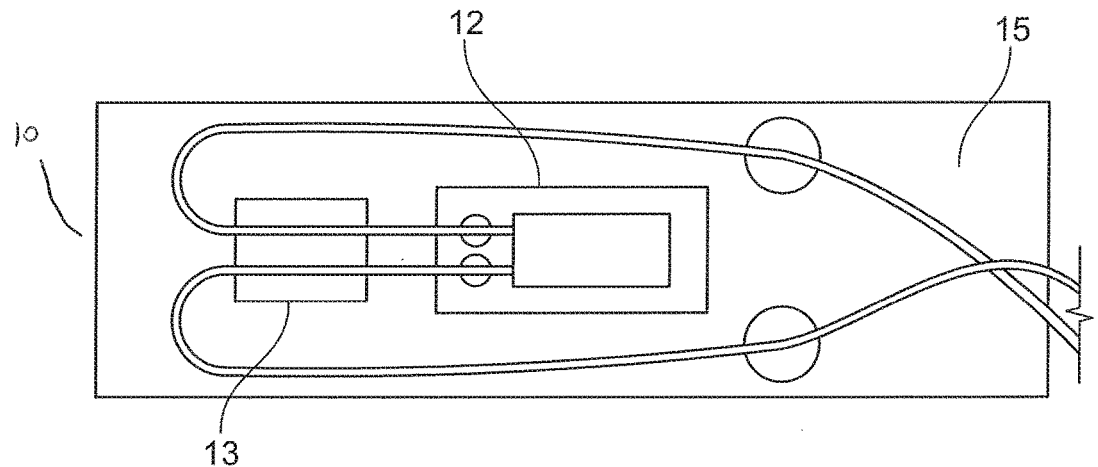
FIG. 5 illustrates one embodiment of a force sensing unit.

Force sensing unit 10 could be a strain gauge, a piezoelectric sensor, an elastoresistive resistor, or another appropriate force sensing device. Strain gauges convert a mechanical change in force to a change in resistance. In one embodiment, illustrated in FIG. 5, force sensing unit 10 is a linear strain gage and comprises a thin copper wire 12 printed on an insulated flexible backing, which is glued to a strain gauge bar 15 with an appropriate adhesive, such as cyanoacrylate. In one embodiment, the strain gauge bar 15 is made of a hard metal, such as steel. Deformation of strain gauge bar 15 results in deformation of the copper wire 12, and the change in cross-sectional area causes a change in the resistance of the strain gauge wire. A commercially available strain gauge may be used, such as model SGD-6/120-LY11 from Omega Engineering (Stamford, Conn.). Force sensing unit 10 may have terminal pads 13 that attach the ribbon of the strain gauge wires 12 to heavier instrumentation wires. Terminal pads 13 prevent force sensing unit 10 from being damaged by stress on the connection wires. Terminal pads 13 are attached to the strain gauge bar 15 using ethyl-based cyanoacrylate glue or another appropriate adhesive. The embodiment of the force sensing unit 100 described above can measure a pretension force of between 0 to 120 Newtons (its bandwidth) on suture 440, and is sufficiently sensitive to measure a difference in pretension on suture 440 as small as 1 Newton, enabling a surgeon using pretensioner 100 to precisely measure the pretension on suture 440.

Circuit.

Figure 6:
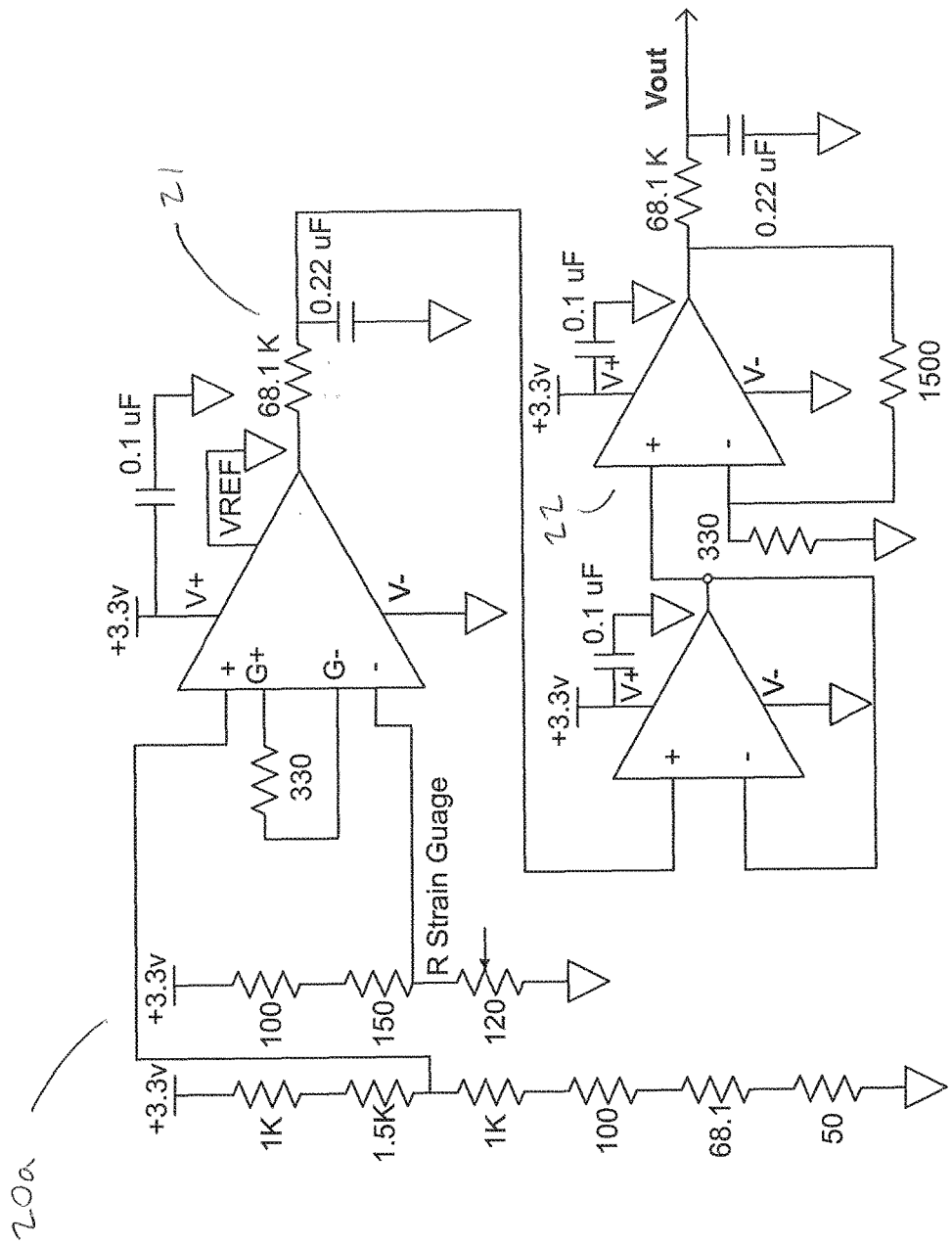
FIGS. 6 and 7 illustrate circuit diagrams of one embodiment of a circuit used with one embodiment of the pretensioner.
Figure 7:
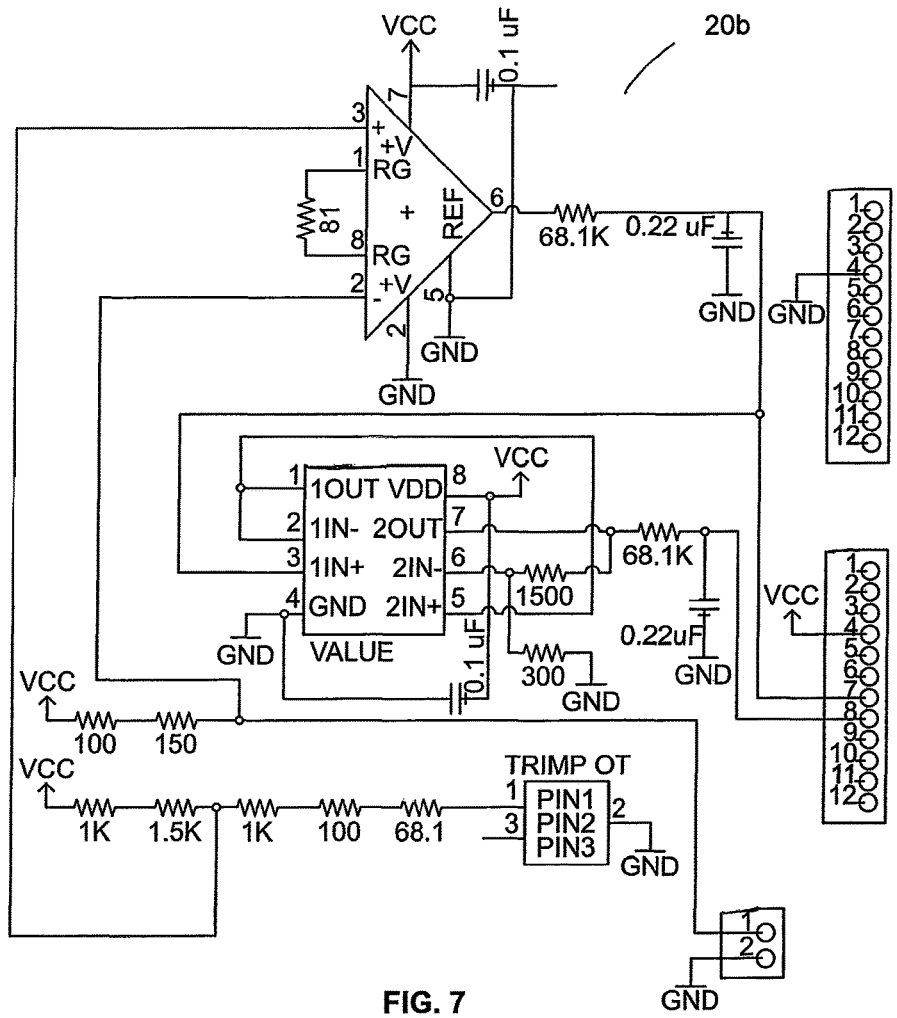

Circuit 20 conditions and amplifies the signal from force sensing unit 10, converting the signal from force sensing unit 10 to a digital signal. In one embodiment, the physical dimensions of circuit 20 are compact, for instance at approximately 0.068"×0.8"×1.4". FIGS. 6 and 7 illustrate circuit diagrams of one embodiment of circuit 20, which comprises circuit portion 20a and 20b and includes an amplifier 22 and low-pass filter 21. Circuit 20 connects directly to microprocessor 60. The output from circuit 20 to microprocessor 60 is an analog signal, and is converted from an analog signal to a digital signal using well-known means.

Microcontroller.

Figure 8:
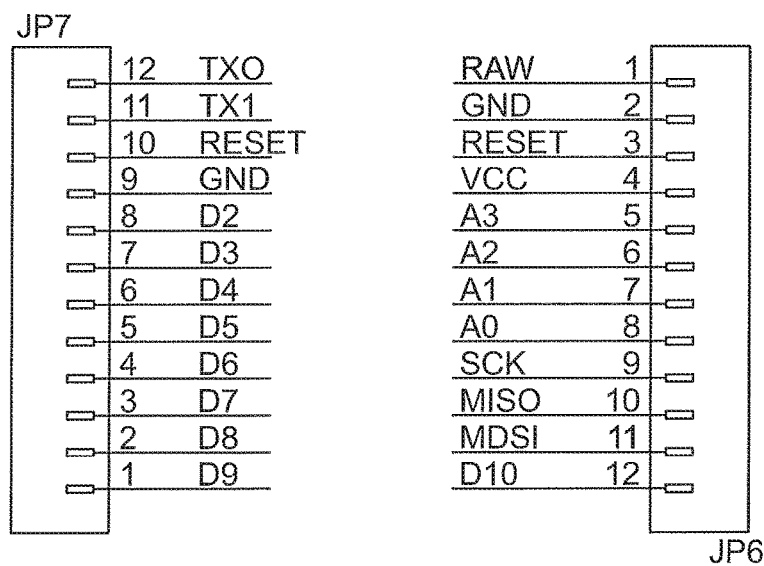
FIG. 8 illustrates the input and output channels of one embodiment of a microcontroller used with one embodiment of the pretensioner.

Pretensioner 100 uses microcontroller 60 to communicate with and transmit data to an external device, such as a tablet or other computing device (not illustrated) for display of the amount of pretension being applied to suture 440. In one embodiment, microcontroller 60 is an Arduino Pro Mini, which has a compact size and an on-board power controller. An Arduino Pro Mini includes an ATMega168 microcontroller chip loaded with the Arduino program environment. FIG. 8 illustrates the input and output channels of one embodiment of microcontroller 60.

Transmitter.

The signal from microprocessor 60 is sent to transmitter 30 for transmission to another device, such as a tablet or other computing device. The computing device may have a display, for display of the pretension value measured by pretensioner 100 and transmitted to the computing device. In one embodiment, transmitter 30 is a Bluetooth modem having an RN-42 Bluetooth module from Roving Networks (Los Gatos, Calif.). In one embodiment, transmitter 30 has a transmission distance of up to 66 feet and transmits on the 2402-2480 MHz range at 1200 bps up to 921 Kbps. Transmitter 30 of a compact size—e.g., with dimensions of dimensions of 0.15"×0.6"×1.9".

Battery.

Pretensioner 100 may further comprise a battery, for powering microcontroller 60, circuit 20, and transmitter 30. In one embodiment, battery 50 is a lithium ion battery that is capable of providing 110 mAh of battery life, provides 3.7V nominal voltage and 0.2 C current. Battery 50 may be from Unionfortune Electronic Co, Ltd. (Guangdong, China) or another manufacturer. In one embodiment, battery 50 is compact, with dimensions of approximately 4 mm×15 mm×28 mm (0.16 inch×0.6 inch×1.1 inch).

Housing.

Figure 9:
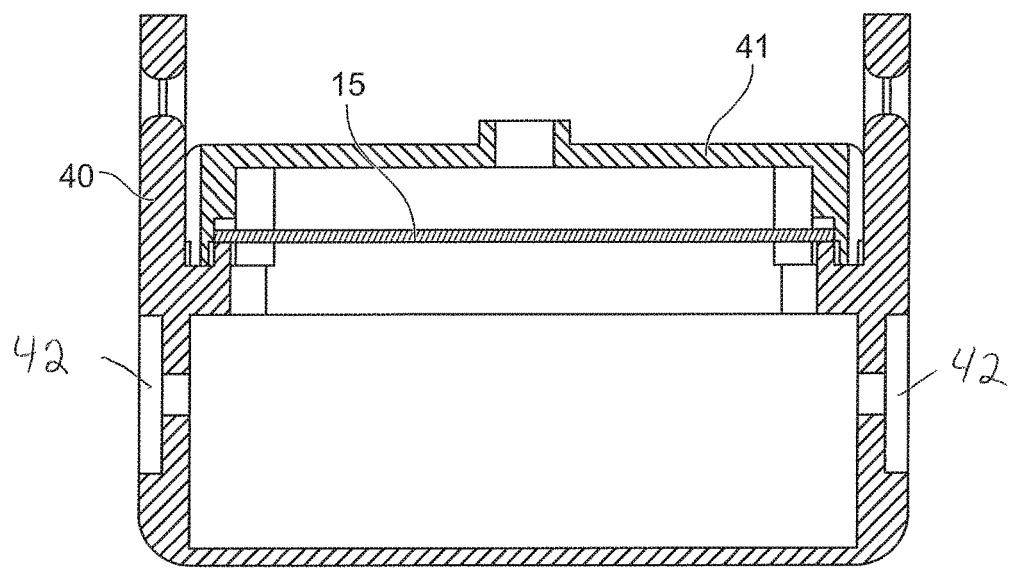
FIG. 9 illustrates a cross sectional view of a housing lid and a strain gauge bar of one embodiment of a pretensioner.

In one embodiment, the housing 40, illustrated in FIG. 4, protects the components of pretensioner 100. FIG. 9 illustrates a cross-sectional view of the strain gauge bar 15 in the housing 40. In one embodiment, housing 40 physically supports the force sensing unit 10, protects the force sensing unit 10 and other electronic components of pretensioner 100 from physical disturbance and contamination, and interfaces with charger 200 (discussed below) to charge battery 50.

Figure 10:
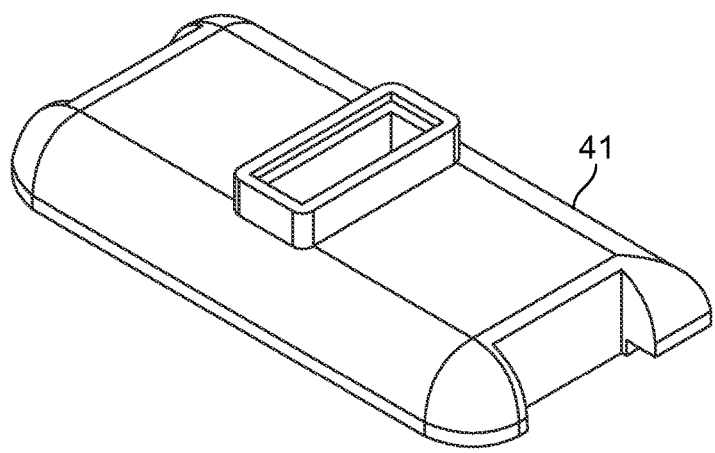
FIG. 10 illustrates one embodiment of a housing unit with an opening for a central post.
Figure 11:
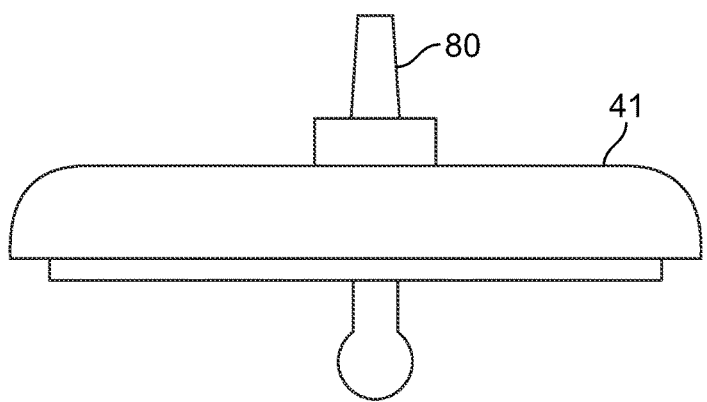
FIG. 11 illustrates a central post partially inserted into a housing lid of one embodiment of the pretensioner.

In one embodiment, force sensing unit 10 is supported in housing lid 41. As illustrated in FIG. 10, housing lid 41 may include an opening for a member, such as center post 80. Center post 80 is rounded at top so that it may be inserted into the opening of housing lid 41. Center post 80 may be flanged at its bottom so that center post 80 cannot be pushed all the way through the opening of housing lid 41. FIG. 11 illustrates center post 80 partially inserted into housing lid 41, and the flange at the bottom of center post 80 can be seen.

In one embodiment, housing lid 41 supports strain gauge bar 15 so that the flanged end of center post 80 applies a moment on strain gauge bar 15 even when pretensioner 100 is not threaded with suture 440. Strain gauge bar 15 may be sized so that it is slightly longer than the length of housing lid 41. Inserting strain gauge bar 15 into housing lid 41, and over the end of the flange of center post 80, results in application of a constant strain on strain gauge bar 15. In this way, a consistent strain is applied to force sensing unit 10 when the pretensioner 100 is at rest, which prevents baseline drift in the signal from force sensing unit 10. FIG. 12 illustrates a photo of strain gauge bar 15 in housing lid 41. Force is applied in the center of strain gauge bar 15 by center post 80.

To permit sterilization of the pretensioner 100, and to protect against bacteria and water entering the housing 40, a silicone seal may be applied to the interface between housing 40 and housing lid 41, and between housing lid 41 and central post 80. The silicone seal still permits the central post 80 to move a small amount in order to impart a variable bending moment on strain gauge bar 15, while preventing contamination of electronic components in force sensing unit 10.

Referring again to FIG. 4, FIG. 4 illustrates the mechanism of force transmission to the force sensing unit 10, where the strain gauge bar 15 is fixed at both ends, and the center post 80 is free to slide through the housing lid 41. In FIG. 4, the white bar represents strain gauge bar 15, the arrows over suture 440 represent force along suture 440, and the arrow 82 represents force vectors on the strain gauge bar 15. As more force is applied to suture 440, the suture pushes down on center post 80, which increases the pretension sensed by force sensing unit 10. FIG. 13A illustrates the electronic components protected within housing 40.

Charger.

Charger 200 charges battery 50 of pretensioner 100 without the user having to open housing 40. One embodiment of charger 200 is illustrated in FIG. 14. Battery 50 may be charged while allowing housing 40 to remain sealed, to help avoid compromising the integrity of the electronics during device sterilization. Current from charger 200 is regulated by a standard charge controller (not illustrated). Charger interfaces with nickel charging plates 42 on either side of housing 40, using nickel plated contacts connected to battery 50. FIG. 15 illustrates pretensioner 100 in charger 200. In one embodiment, charger 200 may be designed so as to prevent pretensioner 100 from being placed in the charger in the wrong configuration. For example, housing 40 may have three rounded corners, and a fourth right angle corner, which are accordingly matched in charger 200, as illustrated in FIG. 14. This allows pretensioner 100 to be placed in charger 200 in only one configuration, preventing incorrect connection of the charging electrodes. The charger may be manufactured using 3D printing or other known manufacturing methods. An LED or other indicator on housing 40 may be used to indicate that pretensioner 100 is sufficiently charged for use.

Pretensioner 100 may also be used in connection with the replacement of other tissues, including the PCL, shoulder tissues that require tissue pretension, and other tissue replacement. Although reference to the pretensioner has been made with respect to its use to measure the tension on a suture, the pretensioner may be used to measure tension in other areas of industrial application, such as the measurement of tension on a cable.

In view of the many possible embodiments to which the principles of the present discussion may be applied, it should be recognized that the embodiments described herein with respect to the drawing figures are meant to be illustrative only and should not be taken as limiting the scope of the claims. Therefore, the techniques as described herein contemplate all such embodiments as may come within the scope of the following claims and equivalents thereof.

We claim:

1. A device for measuring the tension applied to a suture, comprising:
    a metal bar having a top surface and a bottom surface;
    a member comprising a first end and a second end, the member being positioned perpendicular to the top surface of the metal bar so as to apply through its first end an initial pre-determined constant tension to a point on the top surface of the metal bar when a tension is not applied to the suture;
    the member configured to engage at its second end at a first point with the suture;
    a housing for the metal bar, wherein the housing comprises an opening for insertion of the member,
    wherein the second end of the member is sized to prevent removal of the second end of the member through the opening of the housing; and
    a sensor for detecting an amount of deformation of the metal bar, wherein a tension applied to the suture causes the member to deform the metal bar.

2. The device of claim 1, wherein the member is configured to deform the metal bar by pushing against the metal bar at its first end and in response to tension applied to the suture.

3. The device of claim 2, wherein the sensor is positioned on a side of the metal bar opposite from the position of the first end of the member.

4. The device of claim 1, wherein the sensor comprises a strain gauge.

5. The device of claim 1, wherein the first end of the member is sized to permit removal of the first end of the member through the opening of the housing.

* * * * *